United States Patent
Ha et al.

(10) Patent No.: US 11,492,654 B2
(45) Date of Patent: Nov. 8, 2022

(54) METHOD FOR MEASURING PROTEIN KINASE ACTIVITY AND KIT FOR SAME

(71) Applicants: AMOGREENTECH CO., LTD., Gyeonggi-do (KR); KANGWON NATIONAL UNIVERSITY UNIVERSITY—INDUSTRY COOPERATION FOUNDATION, Gangwon-do (KR)

(72) Inventors: Kwon-Soo Ha, Gangwon-do (KR); Deok-Hoon Kong, Gangwon-do (KR)

(73) Assignees: Kangwon National University University-industry Cooperation Foundation, Gangwon-do (KR); AMOLIFESCIENCE CO., LTD., Seoul (KR)

( * ) Notice: Subject to any disclaimer, the term of this patent is extended or adjusted under 35 U.S.C. 154(b) by 1424 days.

(21) Appl. No.: 15/123,859

(22) PCT Filed: May 13, 2014

(86) PCT No.: PCT/KR2014/004281
§ 371 (c)(1),
(2) Date: Jan. 19, 2017

(87) PCT Pub. No.: WO2015/133680
PCT Pub. Date: Sep. 11, 2015

(65) Prior Publication Data
US 2017/0183709 A1   Jun. 29, 2017

(30) Foreign Application Priority Data
Mar. 6, 2014   (KR) .......................... 10-2014-0026821

(51) Int. Cl.
*C12Q 1/48* (2006.01)

(52) U.S. Cl.
CPC .................................. *C12Q 1/485* (2013.01)

(58) Field of Classification Search
CPC ........... G01N 33/54353; G01N 33/573; G01N 2440/14; G01N 2333/912
See application file for complete search history.

(56) References Cited

U.S. PATENT DOCUMENTS 6,335,176 B1 * 1/2002 Inglese ................ C07K 1/1072
  435/68.1
6,383,790 B1   5/2002 Shokat
(Continued)

FOREIGN PATENT DOCUMENTS

JP       2004283114 A    10/2004
KR   10-2001-0061545 A    7/2001
(Continued)

OTHER PUBLICATIONS

Pierce Cell Lysis Handbook (2009, retrieved from http://tools.thermofisher.com/content/sfs/brochures/1601757-Cell-Lysis-Handbook.pdf).*
(Continued)

*Primary Examiner* — Changhwa J Cheu
(74) *Attorney, Agent, or Firm* — IceMiller LLP

(57) ABSTRACT

Disclosed is a method of measuring protein kinase activity, including a) attaching GMBS (N-[γ-maleimidobutyryloxy] sulfosuccinimide ester) to a base plate, b) attaching a substrate that reacts with a protein kinase to the base plate having GMBS attached thereto, thus manufacturing a kit for measuring protein kinase activity, c) introducing, to the kit, a mixture of a sample to be analyzed and a buffer including triton X-100, and d) probing phosphorylation of the substrate caused by the protein kinase contained in the sample, thereby measuring the activity of the protein kinase.

14 Claims, 17 Drawing Sheets

Specification includes a Sequence Listing.

(56) References Cited

U.S. PATENT DOCUMENTS

| | | | |
|---|---|---|---|
| 6,548,266 B1* | 4/2003 | Zhang | C12N 9/1205 435/15 |
| 2007/0179091 A1* | 8/2007 | de Sauvage | A61K 31/7088 514/44 R |
| 2008/0124790 A1 | 5/2008 | Yang et al. | |
| 2008/0175757 A1* | 7/2008 | Powell | B01L 3/5085 422/68.1 |
| 2009/0098574 A1 | 4/2009 | Brisson et al. | |
| 2011/0165603 A1* | 7/2011 | Rininsland | G01N 33/6803 435/15 |
| 2015/0045342 A1* | 2/2015 | Sugimoto | A61P 21/00 514/210.18 |
| 2017/0175167 A1 | 6/2017 | Ha et al. | |
| 2019/0376117 A1 | 12/2019 | Ha et al. | |

FOREIGN PATENT DOCUMENTS

| | | |
|---|---|---|
| KR | 10-2003-0036010 A | 5/2003 |
| KR | 10-2003-0036011 A | 5/2003 |
| KR | 10-2005-0054387 A | 6/2005 |
| KR | 10-2008-0006496 A | 1/2008 |
| WO | 2012/145399 A2 | 10/2012 |
| WO | 2015133681 A1 | 9/2015 |

OTHER PUBLICATIONS

Hannun et al. (The journal of Biological Chemistry 1985;vol. 260,No. 18, issue of Aug. 25, pp. 10039-10043).*
Kwon et al. (Mol. Cells, 2009; 27,337-343).*
Jung et al (Analyst 2012,137, p. 3814).*
Inamori et al Anal Chem 2008, 80, 643-650).*
Jae-Wan Jung et al., "Label-free and quantitative analysis of C-reactive protein in human sera by tagged-internal standard assay on antibody arrays," Biosensors and Bioelectronics, vol. 24, 2009, pp. 1469-1473.
Daniel Korr et al., "LRRK1 protein kinase activity is stimulated upon binding of GTP to its Roc domain," Cellular Signalling, vol. 18, 2006, pp. 910-920.
Cho et al., "Extracellular protein kinase A as a cancer biomarker: Its expression by tumor cells and reversal by a myristate-lacking Ca and RII/b subunit overexpression" PNAS, vol. 97, No. 2, Jan. 18, 2000, pp. 835-840.
Wang, Z., et al., "Microarray-Based Detection of Protein Binding and Functionality by Gold Nanoparticle Probes," 2005, Analytical Chemistry, 77(17), pp. 5770-5774.
Macala, L., et al., "Measurement of cAMP-dependent protein kinase activity using a fluorescent-labeled Kemptide," 1998, Kidney International, vol. 54, pp. 1746-1750.

* cited by examiner

METHOD FOR MEASURING PROTEIN KINASE ACTIVITY AND KIT FOR SAME

CROSS-REFERENCE TO RELATED APPLICATIONS

This application is a National Stage of International patent application PCT/KR2014/004281, filed on May 13, 2014, which claims the benefit of Korean Patent Application No. 10-2014-0026821, filed Mar. 6, 2014, which are hereby incorporated by reference in their entirety into this application.

SEQUENCE LISTING

The instant application contains a Sequence Listing which has been submitted electronically in ASCII format and is hereby incorporated by reference in its entirety. Said ASCII copy, created on Feb. 10, 2017, is named 087248_003460_SL.txt and is 674 bytes in size.

TECHNICAL FIELD

The present invention relates to a method of measuring protein kinase activity, a kit for use therein, and a method of manufacturing the kit.

BACKGROUND ART

A protein kinase is an enzyme that enables a phosphate group to be covalently bonded to tyrosine, serine, and threonine residues on a specific sequence of a substrate protein. In order to assay the activity of protein kinase, the phosphorylation procedures of different protein substrates have to be measured. Also, since over 500 various kinds of protein kinase are provided, on-chip activity assay becomes problematic. Thus, a variety of methods of measuring the activity of enzymes such as protein kinase and the like have been devised, but suffer in that assays and devices that must be used are expensive. Furthermore, although enzyme activity assay methods that are performed on a plate are provided, the procedure for immobilizing a substrate protein is complicated, and structural changes to the substrate protein are caused during the chemical bonding process, undesirably resulting in decreased activity.

Meanwhile, cyclic AMP (cAMP)-dependent PKA (Protein Kinase A) is the most important enzyme for post-transcriptional modification, and plays an important role in a variety of biological procedures, such as cell proliferation, metabolism, gene induction, angiogenesis, the regulation of ion channels, and apoptosis. Such PKA activity is often measured using radioactive isotope-labeled ATP, but typical methods are known to have deficiencies such as the risk of radiation, complications, excessive time consumption and the like. With the goal of overcoming these deficiencies, alternative non-radioactive methods based on fluorescence, luminescent nanoparticles and a quartz crystal microbalance have been proposed. In the fluorescence detection methods, molecular probes such as biotinylated phosphate-specific ligands based on a $Zn^{2+}$ complex and pro-Q diamond dyes are used. Various types of nanoparticles, such as gold nanoparticles, quantum dots, and zirconium ion-immobilized magnetic nanoparticles, have been utilized to improve the sensitivity of PKA activity assays. However, such methods are problematic because limitations are imposed on cost-effectiveness for determining sensitivity and/or kinase activity. Thus, there is a need to develop an assay method for evaluating PKA activity in a manner that is highly sensitive, easy, and economically feasible.

DISCLOSURE

Technical Problem

A first object of the present invention is to provide a method of measuring protein kinase activity having high sensitivity and specificity.

A second object of the present invention is to provide a kit for measuring protein kinase activity that is used for the above method of measuring protein kinase activity.

A third object of the present invention is to provide a method of manufacturing the kit for measuring protein kinase activity.

Technical Solution

The present invention provides a method of measuring protein kinase activity, comprising: a) attaching GMBS (N-[γ-maleimidobutyryloxy]sulfosuccinimide ester) to a base plate, b) attaching a substrate that reacts with a protein kinase to the base plate having GMBS attached thereto, thus manufacturing a kit for measuring protein kinase activity, c) introducing, to the kit, a mixture comprising the sample to be analyzed and a buffer including TRITON X-100 (2-[4-(2,4,4-trimethylpentan-2-yl)phenoxy]ethanol, hereinafter "TRITON X-100"), and d) probing phosphorylation of the substrate caused by the protein kinase contained in the sample, thereby measuring the activity of the protein kinase.

In addition, the present invention provides a kit for measuring protein kinase activity, which is used for the above method of measuring protein kinase activity.

In addition, the present invention provides a method of manufacturing a kit for measuring protein kinase activity, comprising: attaching GMBS (N-[γ-maleimidobutyryloxy]sulfosuccinimide ester) to a base plate, and attaching a substrate that reacts with a protein kinase to the base plate having GMBS attached thereto.

Advantageous Effects

According to the present invention, a method of measuring protein kinase activity is used, whereby protein kinase activity can be measured in a manner that is highly sensitive, easy, and economically feasible.

DESCRIPTION OF DRAWINGS

FIGS. 1B to 1E show the test results for optimizing on-chip PKA activity assays, in which FIGS. 1B to 1D illustrate the results of PKA activity based on the fluorescence intensity of array spots, measured after the reaction mixture, comprising kemptide (b), $MgCl_2$ (c) and ATP (d) at various concentrations and 100 U/mL human cPKA in the reaction buffer, is applied on a well-type peptide array and then incubated for a predetermined period of time, and FIG. 1E illustrates the results of PKA activity based on the fluorescence intensity of array spots, measured after 1 μL aliquots of the reaction mixture including 0.5 mmol/L $MgCl_2$, 0.5 mmol/L ATP, and 100 U/mL human cPKA are applied on a peptide array and then incubated for a predetermined period of time, the results being expressed as an average of three independent test values±SD;

FIGS. 2A to 2F show the high sensitivity of an on-chip PKA activity assay by triton X-100 and an inhibition assay using PKI, in which FIGS. 2A to 2C illustrate the results of PKA activity, measured after the reaction mixture containing triton X-100 and 100 U/mL human cPKA at predetermined concentrations is loaded on a peptide array at 30° C. for 90 min, and specifically, FIG. 2A is a graph showing the dose-dependent increase in sensitivity of on-chip PKA activity assay by triton X-100, FIG. 2B is a graph showing the dose-dependent increase of PKA activity of human cPKA in the presence or absence of 0.01% triton X-100, FIG. 2C is a graph showing the limit of detection (LOD), FIG. 2D illustrates the test results of inter-array reproducibility in the measurement of PKA activity according to the present invention, FIG. 2E illustrates the test results of inter-spot reproducibility in the measurement of PKA activity according to the present invention, and FIG. 2F is a graph showing the dose-dependent inhibition of PKA activity by PKI, wherein the reaction mixture including PKI at a predetermined concentration is applied on the peptide array in the presence of 100 U/mL human cPKA and the PKA activity is then measured and represented as a percentage, the results being expressed as the average of three independent test values±SD;

FIG. 3A illustrates representative fluorescence array images, FIG. 3B illustrates the standard curve ($r^2$=0.99) made from the array images of FIG. 3A, and FIG. 3C is a graph showing the sPKA activity distribution in box plots, each box representing the upper and lower quartiles of sPKA activity and the horizontal line of each box showing the median;

FIGS. 4A and 4B show the ROC plots of sPKA activity for a serological cancer marker, in which FIG. 4A illustrates the ROC curves of the AUC, sensitivity and specificity of sPKA for each kind of cancer after ROC analysis of hepatic cancer patients (n=30), gastric cancer patients (n=30), lung cancer patients (n=30), and colorectal cancer patients (n=30), and FIG. 4B illustrates the ROC curves of cancer patients (n=120) from which AUC and cut-off values are measured to be 0.966 and 3.5 U/mL, respectively;

FIG. 5B illustrates results in which human cPKA at a predetermined concentration is applied on an amine-modified array and the binding thereof to rabbit anti-human cPKA is analyzed using alexa546-conjugated anti-rabbit IgG, FIG. 5C is a graph showing the improved binding of anti-human cPKA, achieved by activating human cPKA, wherein 50 µg/mL human cPKA is pre-incubated with PBS (non-activated) or an activity assay buffer (activated) and then applied on the well-type amine array for 60 min, after which the array is incubated with rabbit anti-human cPKA at a predetermined concentration and probed with alexa546-conjugated anti-rabbit IgG, the results being expressed as the average of three independent test values±SD, FIG. 5D illustrates the results of testing of inter-array reproducibility in the measurement of an sPKA autoantibody level according to the present invention, and FIG. 5E illustrates the results of testing of inter-spot reproducibility in the measurement of PKA activity according to the present invention; FIG. 6A illustrates the fluorescence array images obtained by analyzing sPKA autoantibody levels in human sera from normal individuals (n=30), hepatic cancer patients (n=30), gastric cancer patients (n=30), lung cancer patients (n=30) and colorectal cancer patients (n=30), using a human cPKA protein array, FIG. 6B illustrates the sPKA autoantibody distribution of human sera in box plots, FIG. 6C illustrates the correlation between an sPKA autoantibody and sPKA activity in human serum, and FIG. 6D illustrates the ROC plot of an sPKA autoantibody assay for four kinds of cancer.

BEST MODE

Figure 1A:
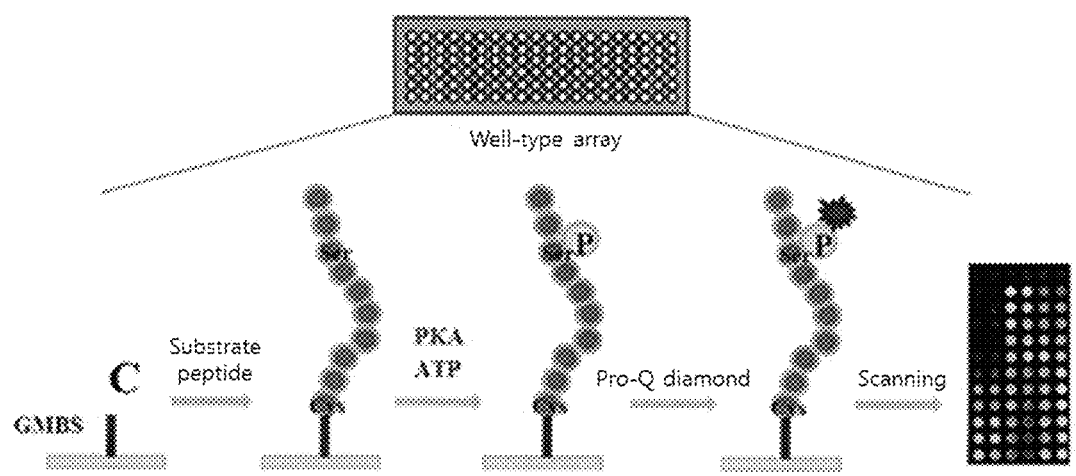
FIG. 1A schematically shows an on-chip PKA activity assay (GMBS, N-[γ-maleimidobutyryloxy]sulfosuccinimide ester; Ser, serine; Cys, cysteine)

The present invention pertains to a method of measuring protein kinase activity, a kit for use therein and a method of manufacturing the kit.

Specifically, the method of measuring protein kinase activity according to the present invention includes the steps of a) attaching GMBS (N-[γ-maleimidobutyryloxy]sulfosuccinimide ester) to a base plate, b) attaching a substrate that reacts with a protein kinase to the base plate having GMBS attached thereto, thus manufacturing a kit for measuring protein kinase activity, c) introducing, to the kit, a mixture comprising the sample to be analyzed and a buffer including triton X-100, and d) probing phosphorylation of the substrate caused by the protein kinase contained in the sample, thereby measuring the activity of the protein kinase.

In the present invention, the protein kinase may be selected from the group consisting of PKA (protein kinase A), Aurora kinases (BTAK, STK15), tyrosine kinase (Lyn), PTK (protein tyrosine kinase), MAPK (MAP kinase), MAPKK (MAP kinase kinase), PKC (protein kinase C), ERK (extracellular signal-regulated kinase), CAMKII (calcium/calmodulin-dependent protein kinase), MEKK (MAP/ERK kinase kinase), JNK (c-Jun N-terminal kinase), SAPK (stress-activated protein kinase), p38K (p38 kinase), phosphatase 2B, serine kinase IKKβ, Ab1K (Ab1 kinase), BTK (Bruton's tyrosine kinase), CDK (cyclin-dependent kinase), VEGF-RTK (Vascular endothelial growth factor-receptor tyrosine kinase), AKT1 kinase, AKT2 kinase, AKT3-kinase, PK (Pyruvate kinase), and tumor M2-pyruvate kinase. Particularly useful is PKA (protein kinase A).

Hereinafter, steps of the method according to the present invention are specified below.

a) Attaching GMBS (N-[γ-Maleimidobutyryloxy]Sulfosuccinimide Ester) to Base Plate In the present invention, GMBS is useful as a linker for connecting a base plate and a substrate that reacts with a protein kinase. Specifically, the N-hydroxysuccinimidyl ester and the maleimide moiety of GMBS may be bound to the base plate and the cysteine residue of the substrate, respectively.

The base plate may be a glass slide, and is preferably an amine-modified glass slide. The amine-modified glass slide may be manufactured by immersing a glass slide in an ethanol solution containing 3-aminopropyltrimethoxiysilane and then firing it.

Also, the base plate may be manufactured by mounting a PDMS (poly(dimethylsiloxane)) gasket on the amine-modified glass slide, but the present invention is not limited thereto.

b) Attaching Substrate, Reacting with Protein Kinase, to Base Plate Having GMBS Attached Thereto to Manufacture Kit for Measuring Protein Kinase Activity The substrate, reacting with the protein kinase, may include, but is not limited to, at least one selected from among kemptide, RelA (NF-kappa-B p65 subunit), RhoA (ras homolog gene family, member A; Rho family GTPase), and CREB (cAMP response element-binding protein).

The substrate, reacting with the protein kinase, is preferably kemptide, and more preferably 0.5 to 10 μg/mL kemptide.

c) Introducing Mixture Comprising Sample to be Analyzed and Buffer Including Triton X-100 to Kit In the present invention, the sample to be analyzed is an unknown candidate to be evaluated to determine whether it affects the diagnosis, treatment or prevention, and metastasis inhibition of disease. Examples of the sample may include, but are not limited to, blood, sera, chemicals, natural extracts, nucleotides, antisense-RNA and the like.

The buffer may further include $MgCl_2$ and ATP, and preferably further includes 0.05 to 0.5 mmol/L $MgCl_2$ and 0.001 to 0.5 mmol/L ATP.

d) Probing Phosphorylation of Substrate Caused by Protein Kinase Contained in Sample to Measure Activity of Protein Kinase The phosphorylation may be probed with an antibody for recognizing a phosphate group, a chemical for recognizing a phosphate group, or a method employing luminescence, but the present invention is not limited thereto. The chemical for recognizing the phosphate group may be a molecular probe such as a biotinylated phosphate-specific ligand based on a $Zn^{2+}$ complex, and particularly Phos-tag.

The phosphorylation may be probed using ELISA, western blotting, flow cytometry, immunofluorescence, immunohistochemistry or mass spectrometry, but the present invention is not limited thereto.

In particular, this step is a process of introducing the kit with a pro-Q diamond stain to thereby probe the serine residue of the substrate, phosphorylated by the protein kinase contained in the sample.

For example, as in the testing of the examples of the present invention, the kit for cancer diagnosis may adopt a high-throughput on-chip sPKA activity array. The on-chip sPKA activity array uses a PKA substrate peptide and a small-molecule fluorescent phosphor sensor and exhibits quantitatively high sensitivity, reproducibility, and cost-reduction effects.

In addition, the present invention addresses a kit for measuring protein kinase activity, suitable for use in the method of measuring protein kinase activity. The kit for measuring protein kinase activity according to the present invention may include a base plate, a substrate that reacts with a protein kinase, and GMBS (N-[γ-maleimidobutyryloxy]sulfosuccinimide ester) as a linker for connecting the base plate and the protein kinase. Also, the kit may further include a composition including any one or more kinds of additional ingredients suitable for assay methods, or a solution or device therefor.

In addition, the present invention addresses a method of manufacturing the kit for measuring protein kinase activity. This method includes attaching GMBS (N-[γ-maleimidobutyryloxy]sulfosuccinimide ester) to a base plate, and attaching a substrate, reacting with a protein kinase, to the base plate having GMBS attached thereto. Also, this method may further include an additional step necessary for manufacturing a kit.

According to the present invention, the method of measuring protein kinase activity, the kit for use therein and the method of manufacturing the kit may be utilized in diagnosing a disease that may be detected by measuring protein kinase activity. In particular, the disease may be cancer, and the cancer may include, but is not limited to, at least one selected from among hepatic cancer, gastric cancer, lung cancer, colorectal cancer, esophageal cancer, rectal cancer, prostate cancer, melanoma, thyroid cancer, liposarcoma, bladder cancer, ovarian cancer, and renal cancer.

In the present invention, "diagnosis" means that the presence of a pathological condition or a feature thereof is identified.

MODE FOR INVENTION

A better understanding of the present invention may be obtained via the following examples, which are set forth to illustrate, but are not to be construed as limiting the scope of the present invention.

Reference Example

Chemical Reagent

Used for the present test, 3-aminopropyltrimethoxysilane, BSA, human serum albumin, ATP and H89 were obtained from Sigma-Aldrich (St. Louis, Mo.). Also, PKA peptide inhibitor (PKI) and cPKA were purchased from Biaffin GmbH & Co KG (Kassel, Germany). N-[γ-maleimidobutyloxy]succinimide ester (GMBS) was obtained from Pierce (Rockford, Ill.). As the PKA substrate peptide, kemptide (C-G-G-L-R-R-A-S-L-G), synthesized by Peptron (Daejeon, Korea), was used. A PRO Q Diamond phosphoprotein gel stain and a destaining solution were purchased from Invitrogen (Carlsbad, Calif.). A poly(dimethylsiloxane) (PDMS) solution was obtained from Sewang Hitech (Gimpo, Korea).

Serum Sample

Human serum samples (n=30) obtained from normal individuals and samples obtained from hepatic cancer patients (n=30), gastric cancer patients (n=30), lung cancer patients (n=30) and colorectal cancer patients (n=30) were supplied by the Biobank, Kangwon National University Hospital (which is a member of the National Biobank Korea, Korea), and were stored at −80° C. until use. Testing using human samples was performed with the approval of the Ethics Committee of local labs for human research.

Data Analysis

In order to achieve quantification of the fluorescence intensity and data extraction, ScanArray Express software was utilized. The Origin 6.0 software package (Origin Lab, Northampton, Mass.) was used to conduct t-tests on the two groups. A p value of less than 0.05 was regarded as statistically significant. With the goal of calculating AUC (Area Under Curve), sensitivity and specificity, ROC (Receiver Operating Characteristics) analysis was performed using MedCalc statistical software 11.4.4.0 (Mariakerke, Belgium).

<Example 1> Manufacture of Well-Type Peptide Array and PKA Activity Assay Using the Same

Example 1-1: Manufacture of Well-Type Peptide Array (1) Manufacture of PDMS Gasket 5 g of a PDMS base and 0.5 g of a curing agent were mixed so as to be cloudy with bubbles and then defoamed at room temperature for 30 min, thus preparing a PDMS prepolymer solution. This mixture was poured into a chromium-coated copper mold (Amogreentech, Gimpo, Korea) having an array of poles with a diameter of 1.5 mm and a height of 0.3 mm. The mold was incubated at 84° C. for 90 min, after which a PDMS gasket having an array of wells having a diameter of 1.5 mm was separated therefrom and was then stored on a transparent film until use.

(2) Manufacture of Well-Type Peptide Array

According to a known method (Jung J W, Jung S H, Yoo J O, Suh I B, Kim Y M, Ha K S. Label-free and quantitative analysis of C-reactive protein in human sera by tagged-internal standard assay on antibody arrays. Biosens Bioelectron 2009; 24:35 1469-73), an amine-modified glass slide was prepared. Specifically, a glass slide (75×25 mm) was washed with $H_2O_2/NH_4OH/H_2O$ (1:1:5, v/v) at 70° C. for 10 min. The slide was immersed for 2 hr in a 95% ethanol solution containing 1.5% 3-aminopropyltrimethoxiysilane (v/v) and fired at 110° C.

The PDMS gasket was mounted on the amine-modified glass slide to manufacture a well-type amine array. The amine array was sequentially modified with 5 mmol/L sulfo-GMBS in a 50 mmol/L sodium bicarbonate buffer (pH 7.0) and a 10 µg/mL substrate peptide (8.1 mmol/L $Na_2HPO_4$, 1.2 mmol/L $KH_2PO_4$, pH 7.4) in a phosphate buffer, thereby yielding a well-type amine array. The N-hydroxysuccinimidyl ester and the maleimide moiety of sulfo-GMBS were bound to the amine-modified glass surface of the array and the cysteine residue of the substrate peptide, respectively.

Example 1-2: PKA Activity Assay Using Well-Type Peptide Array (1) On-Chip PKA Activity Assay Using Peptide Array Based on Fluorescence FIG. 1A schematically shows the on-chip PKA activity assay (GMBS, N-[γ-maleimidobutyryloxy]sulfosuccinimide ester; Ser, serine; Cys, cysteine). As shown in FIG. 1A, a PKA activity assay was performed on the well-type peptide array using a PRO Q Diamond stain.

Specifically, the peptide array was blocked at 37° C. for 30 min with 1% BSA in TBS (13.8 mmol/L NaCl and 2 mmol/L Tris-HCl, pH 7.4) containing 0.1% Tween-20, and was then sequentially washed with TBS containing 0.1% Tween-20 and Milli-Q water. 1 µL of a reaction mixture, comprising an activity assay buffer (50 mmol/L Tris-HCl, pH 7.5, 0.5 mmol/L $MgCl_2$, 0.01% Triton X-100, 500 µmol/L ATP and 0.2% human serum albumin) and diluted serum (20-fold), was applied on the peptide array, both in the presence and in the absence of 2 µmol/L PKI, and then incubated at 30° C. for 90 min. Meanwhile, in order to manufacture a standard curve for quantitative measurement of PKA activity, the reaction mixture containing cPKA at various concentrations was applied on the peptide array.

The array was incubated at room temperature for 60 min together with a PRO Q Diamond stain to probe the phosphorylated serine residue of the peptide substrate. The array was washed two times with a destaining solution for 15 min and was then washed two times with Milli-Q water for 5 min. The resulting array was scanned by means of a fluorescence scanner (ScanArray Express GX, Perkin Elmer, Waltham, Mass.) using a laser at 543 nm, and the fluorescence intensity of the array spots thus measured was used to determine PKA activity.

(2) Determination of PKA Activity

For quantitative measurement of PKA activity, a standard curve consisting of a linear fit was made using the Origin program:

$$y=ax+b$$

in the above equation, y is the fluorescence intensity of a sample on the surface of an array, a and b are the slope and the intercept of the linear fit of the standard curve, respectively, and x is the PKA activity. The PKA activity in the serum sample is calculated from the difference in PKA activity between the absence of PKI and the presence of PKI, and is represented in U/mL.

(3) Optimization of on-Chip sPKA Activity Assay Using Peptide Array Based on Fluorescence As shown in FIG. 1A, a high-sensitivity quantitative assay was performed in order to analyze sPKA activity in human serum samples using a PRO Q Diamond phosphor-sensor.

In order to optimize PKA activity assay, the reaction mixture, comprising kemptide, $MgCl_2$ and ATP at various concentrations, was applied on a GMBS-modified well-type array. Specifically, kemptide, $MgCl_2$ and ATP at various concentrations were mixed with 100 U/mL human cPKA in the reaction buffer to prepare the reaction mixture, which was then applied on the well-type peptide array. Also, 1 µL of the reaction mixture, comprising 10 µg/mL peptide, 0.5 mmol/L $MgCl_2$, 0.5 mmol/L ATP, and 100 U/mL human cPKA, was applied on the peptide array and incubated for a predetermined period of time.

Figure 1B:
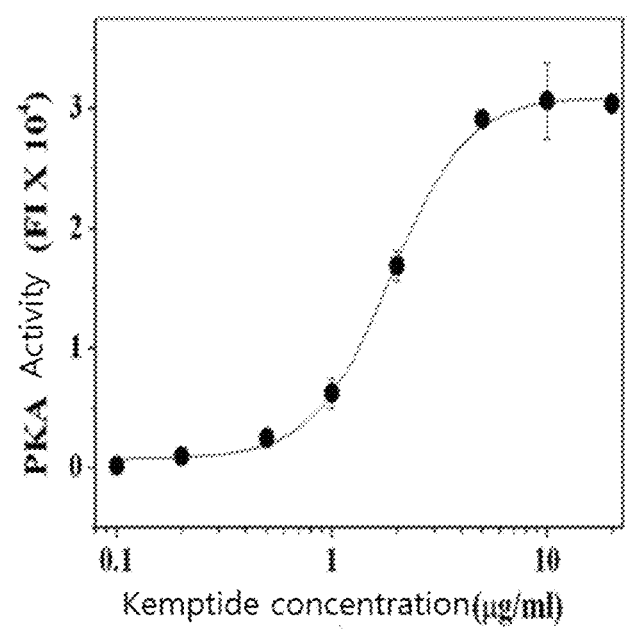
Figure 1C:
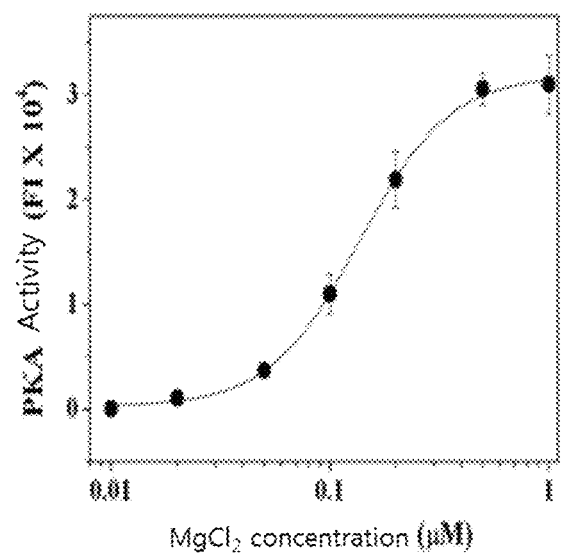
Figure 1D:
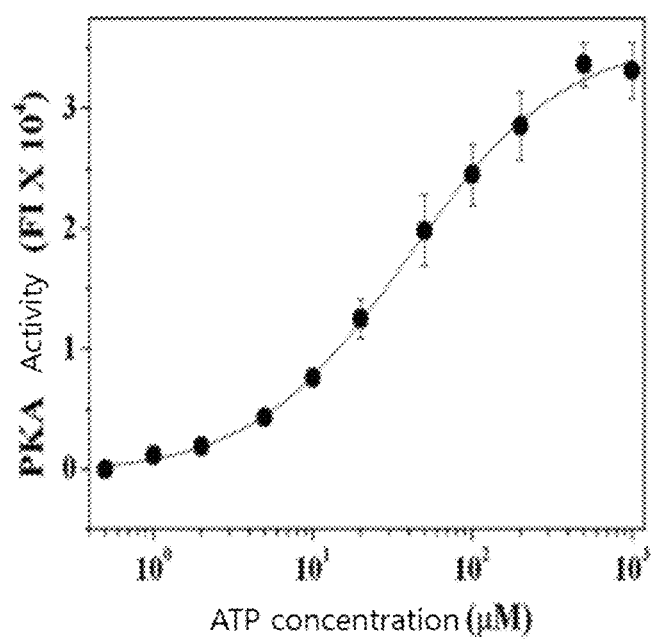
Figure 1E:
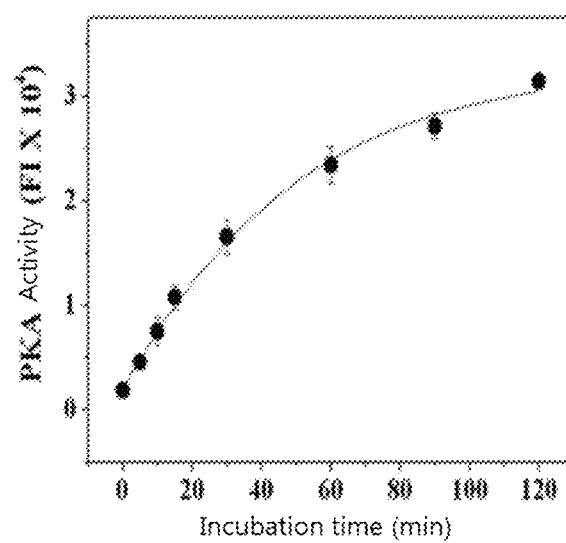

The fluorescence intensity of the array spots was measured using the aforementioned method to determine PKA activity. The results are expressed as the average of three independent test values±SD, and are shown in FIGS. 1B to 1E. As shown in FIG. 1B, the PKA activity, represented by the fluorescence intensity, was increased in a concentration-dependent manner by kemptide, and exhibited maximal effects at 10 µg/mL. $MgCl_2$ also increased the PKA activity in a dose-dependent manner, and was saturated at 0.5 mmol/L (FIG. 1C). ATP increased the PKA activity in a dose-dependent manner, and exhibited maximal stimulation at 0.5 mmol/L (FIG. 1D). The PKA activity was also increased in a time-dependent manner (FIG. 1E).

Figure 2A:
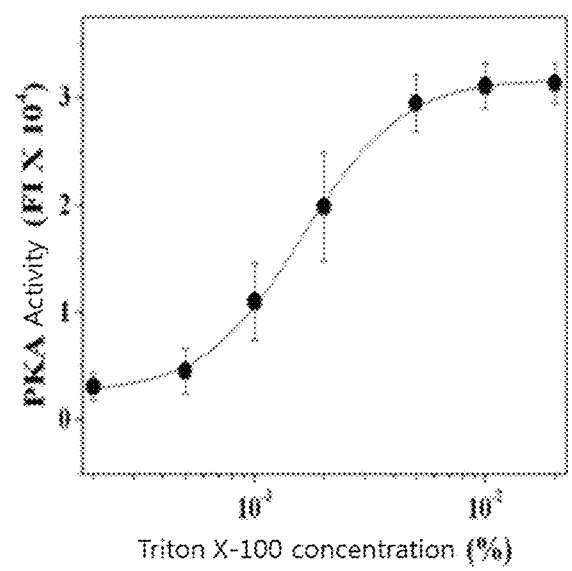
Figure 2B:
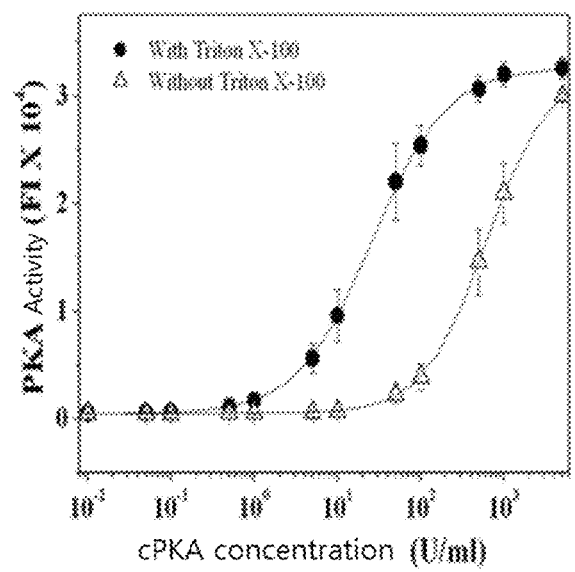
Figure 2C:
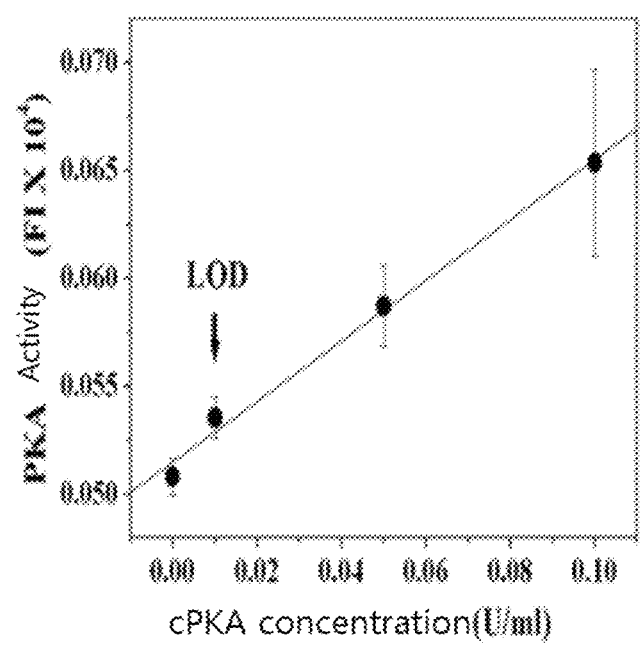

(4) Increase in Sensitivity of on-Chip PKA Activity Assay by Triton X-100 and Characterization of PKA Activity Assay Whether triton X-100 was able to increase the sensitivity of an on-chip PKA activity assay was tested. FIGS. 2A to 2C show the results of measurement of PKA activity after the reaction mixture containing triton X-100 and 100 U/mL human cPKA at predetermined concentrations was loaded on the peptide array at 30° C. for 90 min. As shown in FIG. 2A, triton X-100 increased the PKA activity in a dose-dependent manner, manifested apparent activation at 0.001%, and was saturated at 0.01%. Then, in the presence or absence of triton X-100, the PKA activity of the reaction mixture, containing cPKA at a predetermined concentration, was analyzed, and the effects of triton X-100 on the sensitivity of the PKA activity assay were measured (FIGS. 2B and 2C). Triton X-100 promoted a dose-dependent increase in PKA activity. The limit of detection of the PKA activity assay was increased by 0.01 U/mL from 1.45 using 0.01% triton X-100, from which the PKA activity assay was found to be enhanced by triton X-100.

Using human sera (n=150), inter-array reproducibility and inter-spot reproducibility were analyzed to thus evaluate the reproducibility of the on-chip PKA activity assay.

Figure 2D:
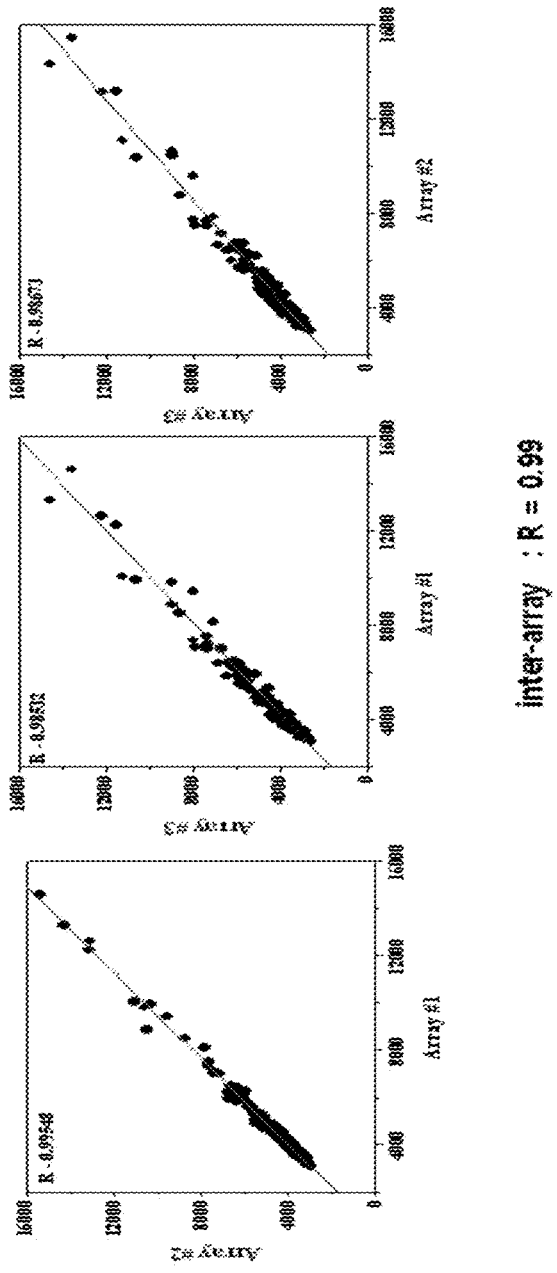
Figure 2E:
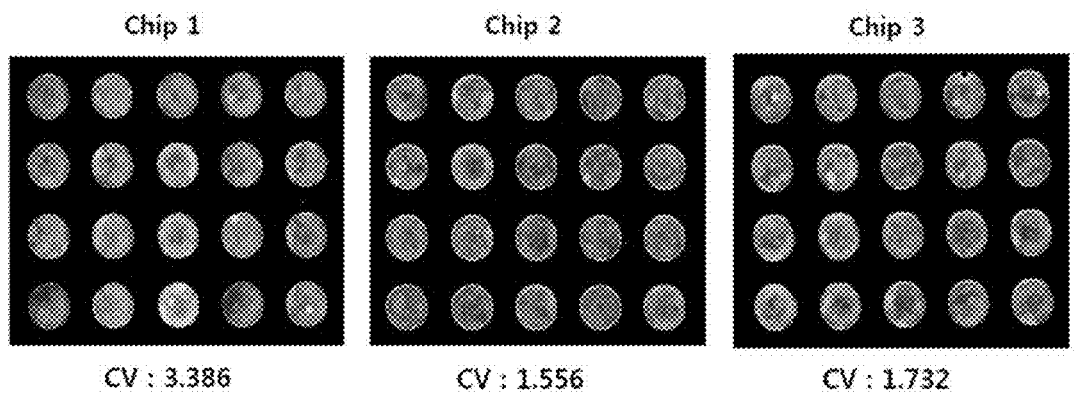

The inter-array reproducibility was determined by analyzing the reaction mixture at the same position on different arrays. The test results are shown in FIG. 2D. As shown in FIG. 2D, the average correlation coefficient was 0.990 (n=3, CV=0.7%), and thus inter-array reproducibility was evaluated to be high. Also, the inter-spot reproducibility was determined by analyzing 20 overlapping spots. The results are shown in FIG. 2E. The average coefficient of variation was 2.2% (n=3). In brief, these results show that the on-chip PKA activity assay exhibits high reproducibility.

Figure 2F:
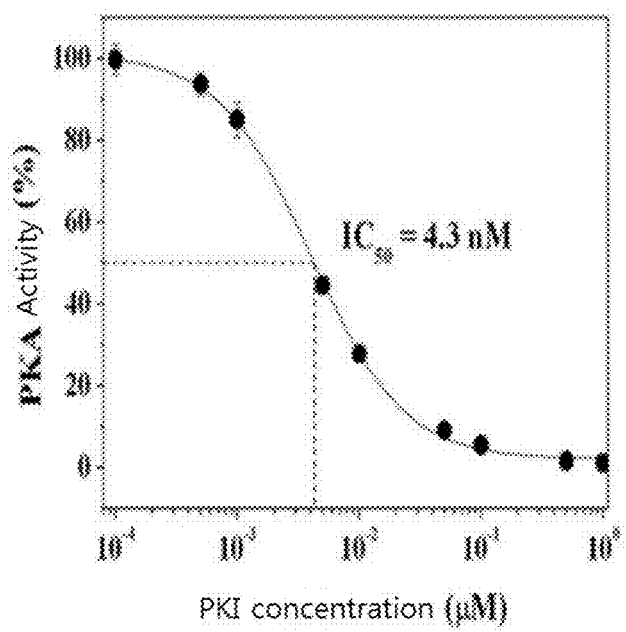

Next, the inhibitory effects on the on-chip PKA activity assay of PKI as the PKA-specific inhibitor were analyzed. FIG. 2F is a graph showing the dose-dependent inhibition of PKA activity by PKI. In the presence of 100 U/mL human cPKA, the reaction mixture containing PKI at a predetermined concentration was applied on the peptide array, and the PKA activity was represented as a percentage. The results are expressed as the average of three independent test values±SD. As shown in FIG. 2F, when 100 U/ml cPKA was used, PKI inhibited PKA activity in a dose-dependent manner, and the maximal effect thereof was exhibited at 0.5 µM. The $IC_{50}$ (half-maximum inhibitory concentration) of PKI on PKA activity assay was calculated to be 4.3 nM. Thereby, specific sPKA activity in the human blood sample can be determined using PKI and the on-chip PKA activity assay is evaluated as being appropriate for screening the PKA inhibitor.

Figure 3A:
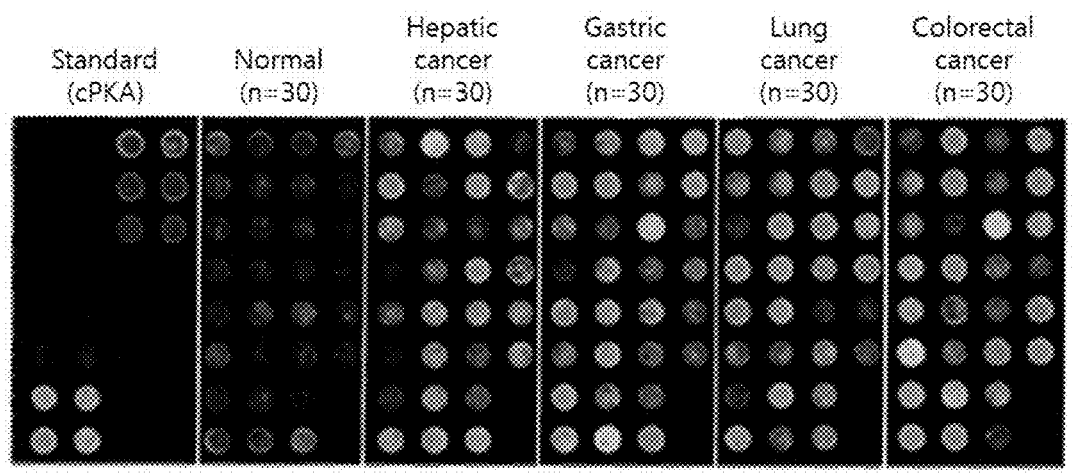
FIGS. 3A to 3C show the results of measurement of sPKA activity of human sera from normal individuals and cancer patients, in which the reaction mixture, including human sera (diluted 20-fold, n=150) from normal individuals (n=30) and hepatic cancer patients (n=30), gastric cancer patients (n=30), lung cancer patients (n=30), and colorectal cancer patients (n=30), is applied on a peptide array and the sPKA activity of 150 serum samples is determined using a standard curve, and specifically.
Figure 3B:
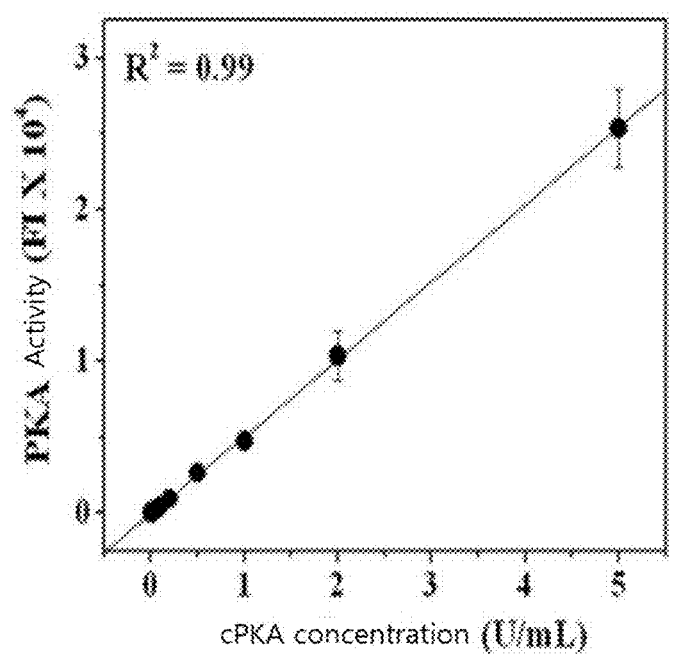

(5) Measurement of sPKA Activity of Human Sera from Normal Individuals and Patients with Four Kinds of Cancer In order to evaluate the activity of sPKA as a cancer biomarker, the following test was performed. Specifically, an on-chip activity assay was performed to determine the sPKA activity of human sera from normal individuals (n=30) and hepatic cancer patients (n=30), gastric cancer patients (n=30), lung cancer patients (n=30) and colorectal cancer patients (n=30). The reaction mixture comprising cPKA at various concentrations and diluted human serum was applied on the peptide array, and phosphorylated serine of kemptide was probed with a PRO Q Diamond stain. The sPKA activity was measured using the standard curve made based on the fluorescence intensity of cPKA (FIGS. 3A and 3B). FIG. 3A illustrates the typical fluorescence array images, and FIG. 3B illustrates the standard curve made from the array images of FIG. 3A ($r^2$=0.99).

Figure 3C:
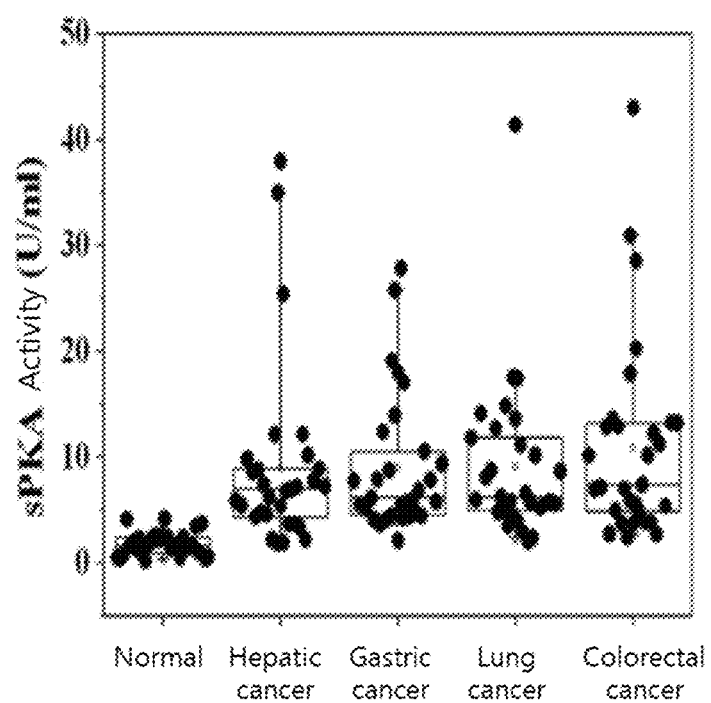

In order to exclude the non-specific signal of anode kinase, sPKA activity in the presence of PKI was subtracted from sPKA activity in the absence of 0.5 µM PKI to thereby determine human serum sPKA activity. The results are shown in the box plots (FIG. 3C). FIG. 3C is a graph showing the sPKA activity distribution in box plots. Each box represents the upper and lower quartiles of sPKA activity. The horizontal line of each box indicates the median. The average sPKA activity values of normal individuals and patients with hepatic cancer, gastric cancer, lung cancer and colorectal cancer were 1.78±1.09, 8.92±8.72, 8.96±6.53, 9.06±7.50 and 10.94±9.34 U/mL, respectively, and the sPKA activity in all cancer patients was much higher than in normal individuals ($p<10^{-4}$). Therefore, the on-chip PKA activity assay is suitable for determining the sPKA activity of human serum, and the sPKA activity can be used as a biomarker for cancer diagnosis.

Figure 4A:
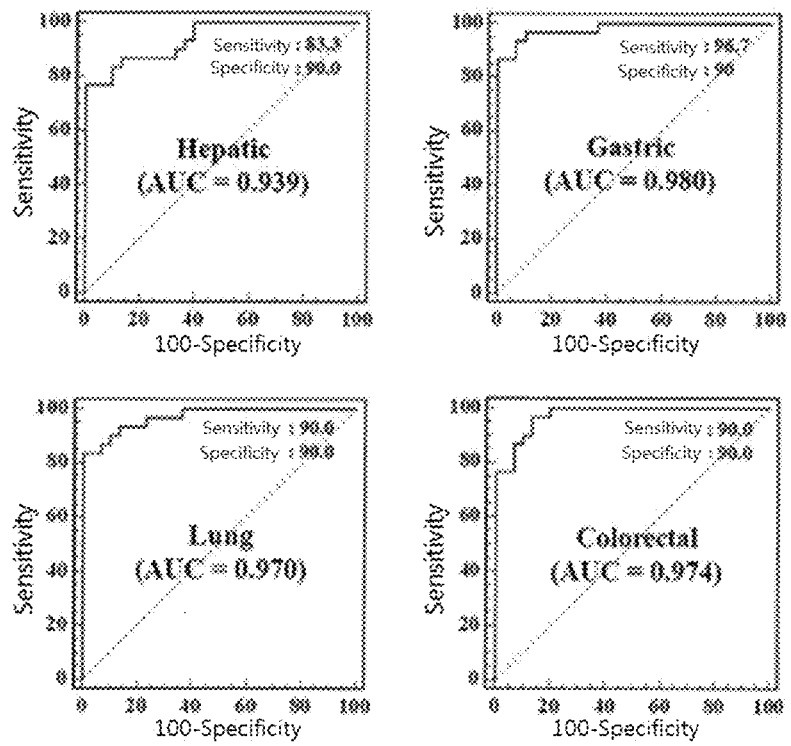

In order to evaluate the activity of sPKA as a cancer biomarker, an on-chip activity assay was performed for four kinds of cancer as described above, and ROC analysis was conducted (FIG. 4A). FIG. 4A shows the ROC curves of AUC, sensitivity and specificity of sPKA for each kind of cancer after the ROC analysis of hepatic cancer patients (n=30), gastric cancer patients (n=30), lung cancer patients (n=30), and colorectal cancer patients (n=30). The results of sensitivity and specificity of sPKA activity obtained for the four kinds of cancer are as follows: hepatic cancer (83.3% and 90.0%), gastric cancer (96.7% and 90%), lung cancer (90.0% and 90.0%), and colorectal cancer (90.0% and 90.0%).

The following high AUC values were obtained: 0.939 (95% confidence interval, 0.85-0.98), 0.980 (95% confidence interval, 0.91-0.99), 0.970 (95% confidence interval, 0.89-0.99) and 0.974 (95% confidence interval, 0.90-0.99).

Figure 4B:
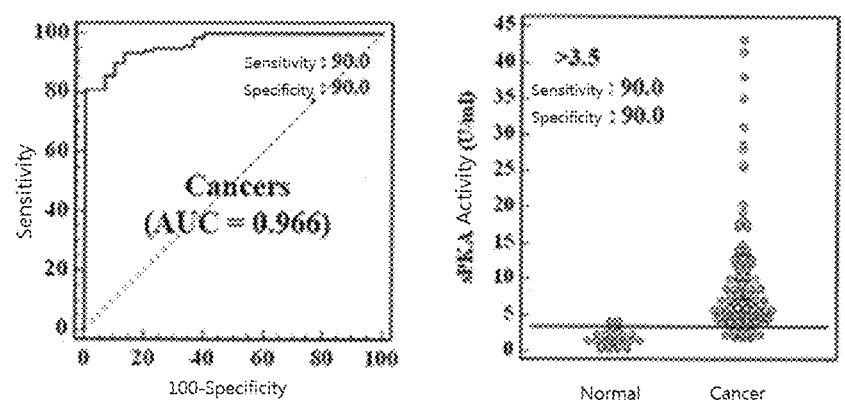

In FIG. 4B, AUC and cut-off values are measured to be 0.966 and 3.5 U/mL, respectively, from the ROC curve of cancer patients (n=120). The sPKA activity assay of all of the cancer patients exhibited a sensitivity of 90.0% and a specificity of 90.0%, and in particular, an AUC value of 0.966 (95% confidence interval, 0.92-0.98) and a cut-off value of 3.5 U/mL were obtained, which are evaluated to be higher than conventionally reported values. Hence, sPKA activity is regarded as a potential biomarker for cancer diagnosis.

Consequently, sPKA activity in human sera of patients with hepatic cancer, gastric cancer, lung cancer and colorectal cancer was much higher than that of the control group. However, there was no significant difference in sPKA autoantibody between the cancer group and the normal group. Furthermore, in human sera, sPKA activity was observed to have no correlation with the sPKA autoantibody level. Thus, sPKA activity, rather than the sPKA autoantibody, is deemed to be suitable for use as a biomarker for cancer diagnosis. Also, the on-chip sPKA activity assay is effective for cancer diagnosis, and has very high potential for use in inhibitor screening and in the diagnosis of PKA-related human diseases.

Figure 5A:
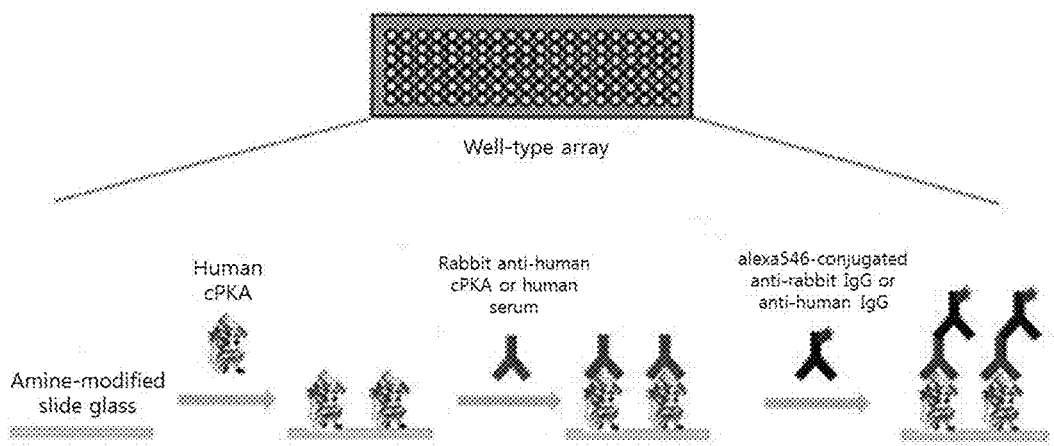
FIGS. 5A to 5E show the optimization of sPKA autoantibody assays using a cPKA protein array, in which FIG. 5A schematically illustrates an sPKA autoantibody assay.

<Comparative Example 1> Manufacture of cPKA Protein Array and Analysis of Human Serum sPKA Autoantibody Level Using the Same (1) Manufacture of Human cPKA Protein Array and sPKA Autoantibody Assay in Human Serum Sample FIG. 5A schematically shows the sPKA autoantibody assay. As shown in FIG. 5A, the human serum sPKA autoantibody level was analyzed using a cPKA protein array. To manufacture the human cPKA protein array, human cPKA was prepared at various concentrations in PBS (8.1 mmol/L $Na_2HPO_4$, 1.2 mmol/L $KH_2PO_4$, pH 7.4, 2.7 mmol/L KCl, and 138 mmol/L NaCl; non-activated) on ice or in an activity assay buffer (activated) and then applied on the well-type amine array at 37° C. for 60 min. The array thus obtained was sequentially washed with PBS containing 0.1% Tween-20 (PBST) for 10 min, and with Milli-Q water for 5 min. The array was blocked at 37° C. for 60 min using 1% BSA in PBST. Rabbit anti-human PKA in PBS containing 0.05% Tween-20 or 20-fold diluted human serum was applied at a predetermined concentration on the human cPKA array at 37° C. for 60 min, and then probed at 37° C. for 60 min using 10 g/mL alexa546-conjugated anti-rabbit IgG or anti-human IgG in PBS containing 0.05% Tween-20 and 1% BSA. The array was washed with PBST for 10 min, further washed with Milli-Q water for 5 min, and dried in air.

Thereafter, the array was scanned by means of a fluorescence scanner using a laser at 543 nm.

(2) Optimization of Serological PKA Autoantibody Assay Using cPKA Protein Array

Figure 5B:
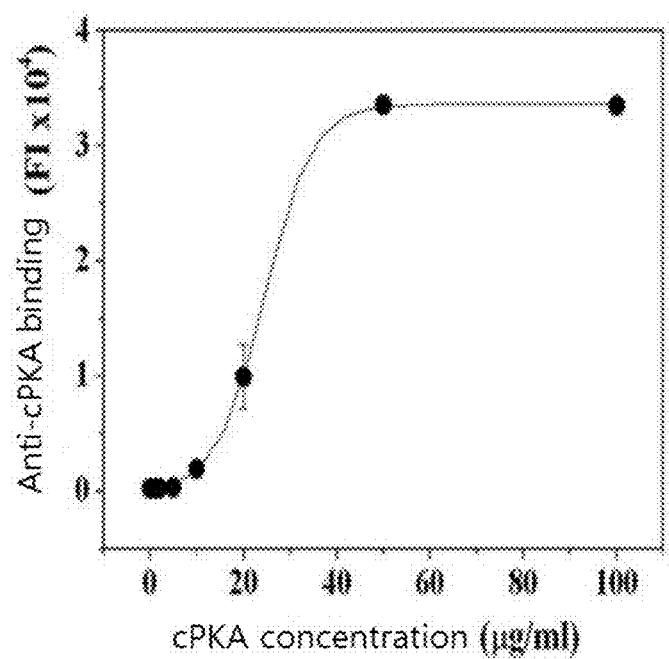

In order to optimize the sPKA autoantibody assay, as shown in FIG. 5A, human cPKA was immobilized at a predetermined concentration on the surface of the well-type amine array, thus manufacturing a protein array, and a reaction mixture including rabbit anti-human cPKA was applied on the cPKA protein array, and the binding thereof to rabbit anti-human cPKA was analyzed through probing with alexa546-conjugated anti-rabbit IgG. FIG. 5B shows the results, in which human cPKA was applied at a predetermined concentration on the amine-modified array and the binding thereof to rabbit anti-human cPKA was analyzed with alexa546-conjugated anti-rabbit IgG. As shown in FIG. 5B, human cPKA increased the binding of anti-human cPKA in a dose-dependent manner, and was saturated at 50 µg/mL.

Figure 5C:
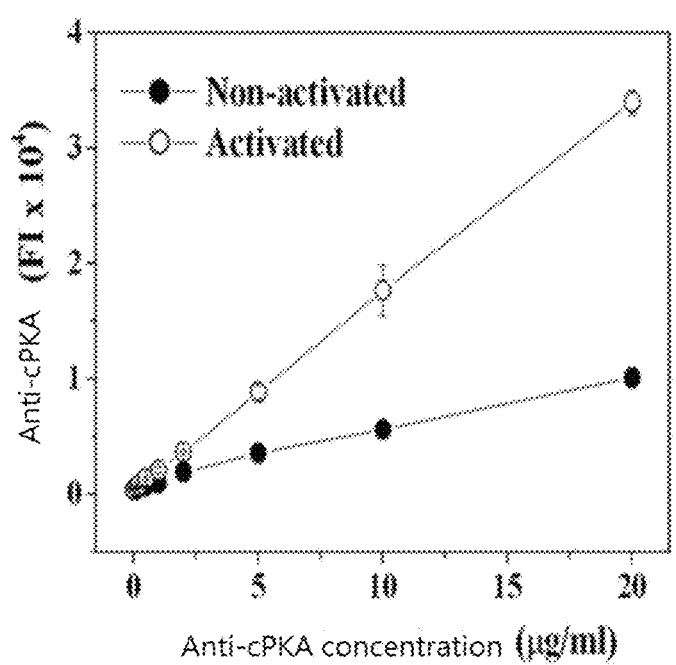

Next, whether the activation of human cPKA with the activity assay buffer was able to increase the binding affinity of anti-human cPKA to cPKA was tested. Human cPKA was pre-incubated with PBS (non-activated) or an activity assay buffer (activated), and was then immobilized onto the well-type amine array, and the binding of anti-human cPKA was analyzed. FIG. 5C is a graph showing the improved binding of anti-human cPKA, achieved by activating human cPKA. As shown in FIG. 5C, the activation of cPKA significantly increased the binding of anti-human cPKA to its antigen. Also, under both of the above two conditions, the binding of anti-human cPKA and human cPKA protein array was linearly proportional up to an antibody concentration of 40 µg/mL.

Figure 5D:
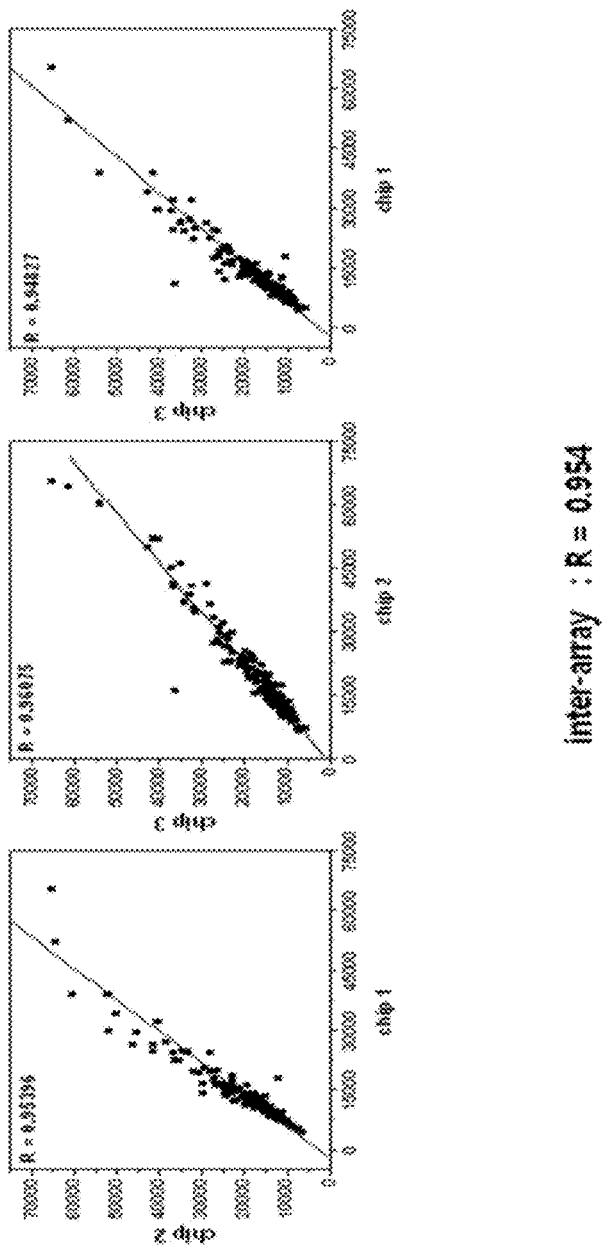
Figure 5E:
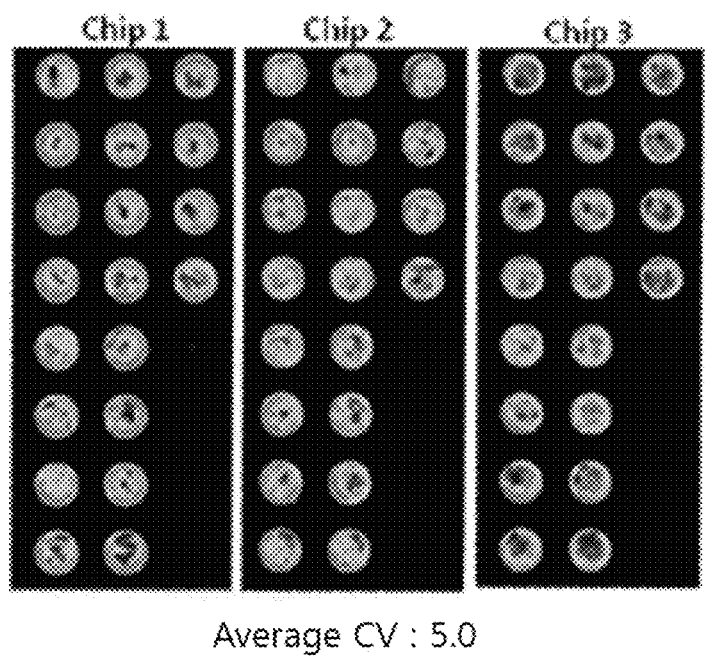

In order to measure the reproducibility of the on-chip PKA assay, inter-array reproducibility and inter-spot reproducibility were tested using the same procedures, and the on-chip sPKA autoantibody assay reproducibility was evaluated using human sera (n=150). The results are shown in FIG. 5D. Based on the test results, the average value (n=3, CV=0.7%) of the correlation coefficient was 0.954, from which inter-array reproducibility was evaluated to be high. Furthermore, the results of evaluation of inter-spot reproducibility are shown in FIG. 5E, where it is evaluated based on a coefficient of variation of 5.0% (n=3). Therefore, the sPKA autoantibody assay using the human cPKA protein array is suitable for use in anti-cPKA assays on human sera.

Figure 6A:
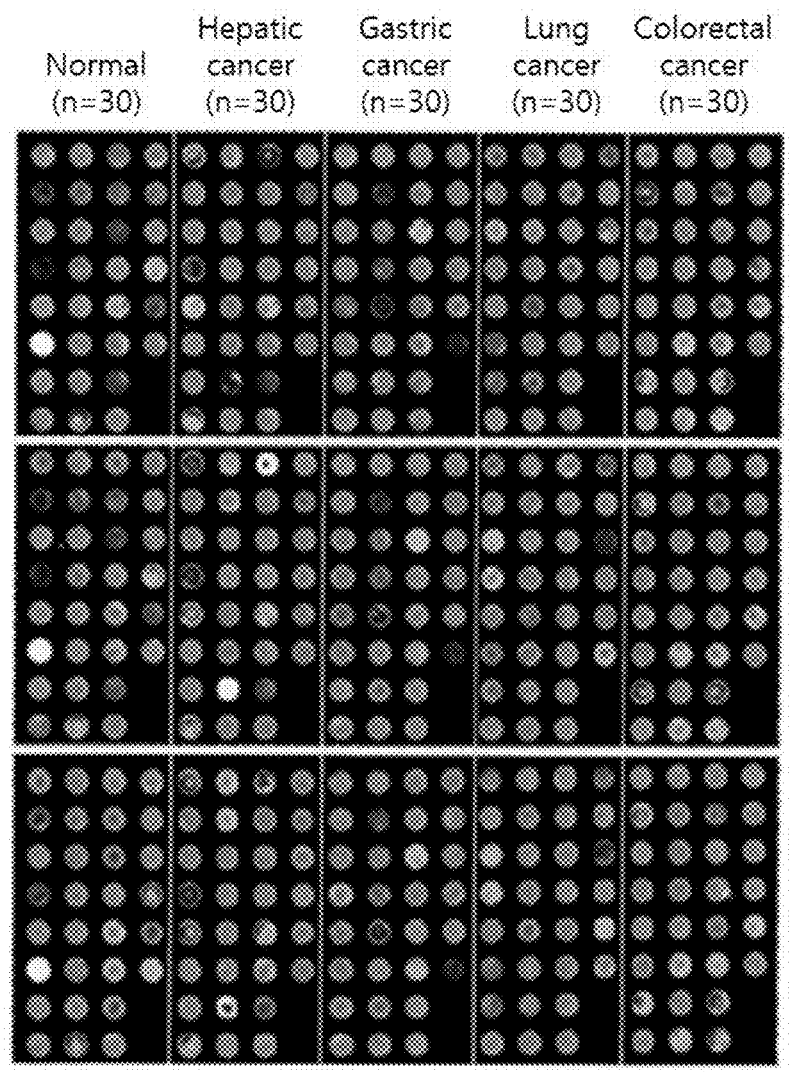
FIGS. 6A to 6D show the results of a serological PKA autoantibody assay in human serum from normal individuals and four kinds of cancer patients, in which human serum (diluted 20-fold) from normal individuals (n=30), as well as hepatic cancer patients (n=30), gastric cancer patients (n=30), lung cancer patients (n=30) and colorectal cancer patients (n=30), is applied on a human cPKA protein array, and the array obtained to detect the sPKA autoantibody is incubated with an alexa546-conjugated anti-human IgG and analyzed with a fluorescence scanner.
Figure 6B:
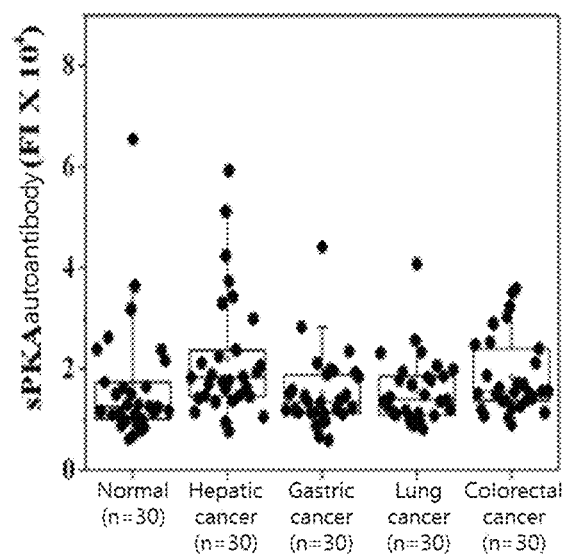

(3) Analysis of Correlation Between sPKA Autoantibody Level in Human Serum Sample and sPKA Activity In order to evaluate the PKA autoantibody as the cancer biomarker, as shown in FIG. 5A, the sPKA autoantibody level in human sera from a normal group (n=30) and a patient group comprising hepatic cancer patients (n=30), gastric cancer patients (n=30), lung cancer patients (n=30) and colorectal cancer patients (n=30) was measured using the human cPKA protein array (FIG. 6A), and was utilized in an sPKA activity assay. FIG. 6B shows the sPKA autoantibody distribution of human sera in box plots. As shown in FIG. 6B, there was no significant difference in PKA autoantibody level between the normal group and the four cancer groups (p>0.05), which means that the PKA autoantibody level is not a good biomarker for cancer diagnosis.

Figure 6C:
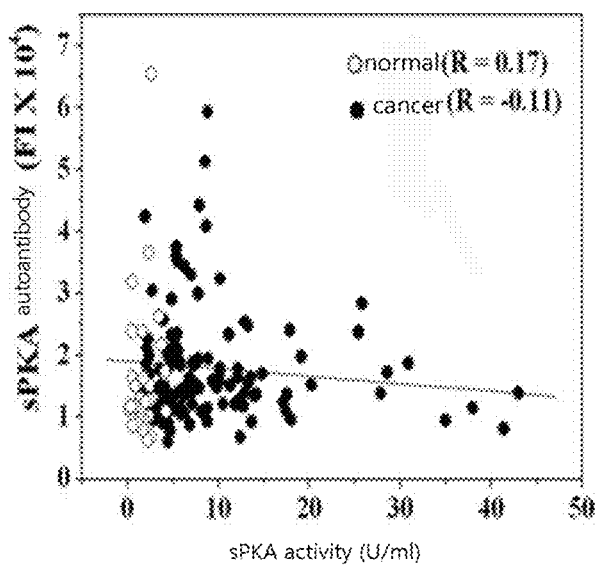
Figure 6D:
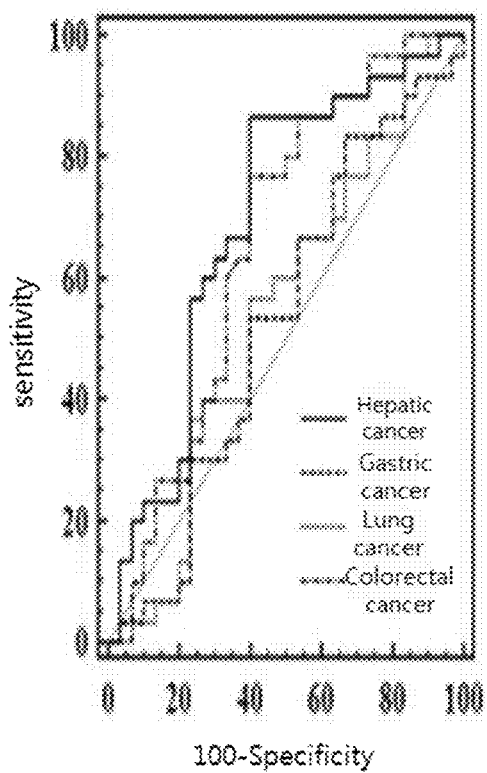

Additionally, the correlation coefficient between PKA autoantibody level and sPKA activity in the sera of normal cells and cancer patients was measured. FIG. 6C shows the correlation between sPKA autoantibody and sPKA activity in human sera. The sPKA activity distribution had no relationship with the PKA autoantibody level distribution, and R values for the normal individuals and the cancer patients were respectively 0.17 and −0.11 (FIG. 6C). FIG. 6D shows the ROC plot of an sPKA autoantibody assay for four kinds of cancer. The AUC, sensitivity and specificity values for each kind of cancer are given in the table. The AUC values of the sPKA autoantibody were 0.698 (hepatic, sensitivity: 86.7%, specificity: 60.0%), 0.526 (gastric, sensitivity: 66.7%, specificity: 46.7%), 0.544 (lung, sensitivity: 56.7%, specificity: 60.0%), and 0.659 (colorectal, sensitivity: 76.6%, specificity: 60.0%), which were observed to be much lower than the values of sPKA activity (FIG. 6D). Also, all of the cancer patients (n=120) exhibited AUC of 0.607, a sensitivity of 68.3%, and a specificity of 60.0%, which were evaluated to be much lower than the values of sPKA activity (FIG. 6D). Based on these results, the sPKA autoantibody level is not regarded as a good biomarker for cancer diagnosis, compared to sPKA activity.

Also, compared to the method of Comparative Example 1 for analyzing the protein kinase through autoantibody assay, the method of measuring the protein kinase activity through phosphorylation of the substrate that reacts with the protein kinase, according to the present invention, has been found to measure protein kinase activity in a manner that is highly sensitive, easy, and economically feasible.

INDUSTRIAL APPLICABILITY

According to the present invention, a method of measuring protein kinase activity is used, whereby protein kinase activity can be measured in a manner that is highly sensitive, easy, and economically feasible.

The invention claimed is:

1. A method of measuring protein kinase activity, comprising:
    a) attaching GMBS (N-[γ-maleimidobutyryloxy]sulfosuccinimide ester) to a base plate;
    b) attaching a substrate that reacts with a protein kinase to the base plate having GMBS attached thereto, thus manufacturing a kit for measuring protein kinase activity;
    c) introducing a mixture comprising a sample to be analyzed and a buffer including (2-[4-(2,4,4-trimethylpentan-2-yl)phenoxy]ethanol) with a concentration of 0.001% to 0.01% into the base plate; and
    d) probing phosphorylation of the substrate caused by the protein kinase contained in the sample, thereby measuring activity of the protein kinase,
    wherein the base plate is an amine-modified glass slide obtained by immersing a glass slide in an ethanol solution including 3-aminopropyltrimethoxysilane and then firing the glass slide,
    wherein the substrate that reacts with the protein kinase is kemptide of SEQ ID NO: 1 comprising cysteine,
    wherein the succinimidyl moiety of the GMBS is linked to the amine of the amine-modified glass slide, and the maleimide moiety of the GMBS is linked to the cysteine residue of the kemptide.

2. The method of claim 1, wherein the base plate is obtained by mounting a PDMS (poly(dimethylsiloxane)) gasket on an amine-modified glass slide.

3. The method of claim 1, wherein the substrate that reacts with the protein kinase is 0.5 to 10 μg/mL kemptide.

4. The method of claim 1, wherein the buffer further includes $MgCl_2$ and ATP.

5. The method of claim 1, wherein the buffer further includes 0.05 to 0.5 mmol/L $MgCl_2$ and 0.001 to 0.5 mmol/L ATP.

6. The method of claim 1, wherein d) comprises introducing the kit with a pro-Q diamond stain to thus probe a serine residue of the substrate, phosphorylated by the protein kinase contained in the sample.

7. The method of claim 1, wherein the phosphorylation is probed with any one selected from among an antibody for recognizing a phosphate group, a chemical for recognizing a phosphate group, and a method employing luminescence.

8. The method of claim 1, wherein the method comprises probing phosphorylation of the substrate via ELISA, western blotting, flow cytometry, immunofluorescence, immunohistochemistry, or mass spectrometry.

9. A kit for measuring protein kinase activity comprising:
    an amine-modified glass slide obtained by immersing a glass slide in an ethanol solution including 3-aminopropyltrimethoxysilane and then firing the glass slide;
    a solution comprising a GMBS (N-[7-maleimidobutyryloxy] sulfosuccinimide ester);
    a kemptide of SEQ ID NO: 1; and
    a buffer including (2-[4-(2,4,4-trimethylpentan-2-yl) phenoxy] ethanol) with a concentration of 0.001% to 0.01%,
    wherein the kit is suitable for use in the method of claim 1.

10. The method of claim 1, wherein the method comprises introducing a mixture comprising the sample to be analyzed and a buffer including (2-[4-(2,4,4-trimethylpentan-2-yl) phenoxy]ethanol) with a concentration of 0.001% to less than 0.01% into the base plate.

11. The method of claim 1, wherein the method measures the activity of Protein Kinase A.

12. The method of claim 11, wherein the method comprises introducing a mixture comprising the sample to be analyzed and a buffer including (2-[4-(2,4,4-trimethylpentan-2-yl)phenoxy]ethanol) with a concentration of 0.001% to less than 0.01% into the base plate.

13. The method of claim 11, wherein the buffer including (2-[4-(2,4,4-trimethylpentan-2-yl)phenoxy]ethanol) promotes a dose-dependent increase in PKA activity.

14. The method of claim 1, wherein the method measures the activity of serine-threonine Protein Kinase A.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gly Gly Leu Arg Arg Ala Ser Leu Gly
1               5                   10
```